United States Patent [19]

Habeger

[11] 4,017,404
[45] Apr. 12, 1977

[54] APPARATUS FOR LOW TEMPERATURE ASHING USING RADIO FREQUENCY EXCITED GAS PLASMA

[75] Inventor: Larry E. Habeger, Big Lake, Minn.

[73] Assignee: The United States of America as represented by the Secretary of the Department of Health, Education and Welfare, Washington, D.C.

[22] Filed: Mar. 11, 1976

[21] Appl. No.: 665,878

[52] U.S. Cl. .......................... 250/531; 23/230 PC; 23/253 PC; 204/164; 250/541
[51] Int. Cl.² .................... B01K 1/00; G01N 27/00
[58] Field of Search ................ 23/230 PC, 253 PC; 204/164; 250/531, 541

[56] References Cited
UNITED STATES PATENTS

| | | | |
|---|---|---|---|
| 2,664,394 | 12/1953 | Reeves | 204/155 |
| 3,671,195 | 6/1972 | Bersin | 23/230 PC |
| 3,720,589 | 3/1973 | Thompson | 250/547 |
| 3,738,828 | 6/1973 | Inoue | 75/211 |
| 3,861,137 | 1/1975 | Russell et al. | 60/39.82 P |

FOREIGN PATENTS OR APPLICATIONS 99,825   9/1940   Sweden .......................... 250/531

*Primary Examiner*—F.C. Edmundson
*Attorney, Agent, or Firm*—John S. Roberts, Jr.; Norman J. Latker; Thomas G. Ferris

[57] ABSTRACT

An apparatus for low temperature ashing of specimens is provided. The specimens to be ashed are first freeze dried and then reduced to an ash by a radio frequency (RF) excited gas plasma in a device which includes a reaction chamber, means to reduce the pressure in the chamber, means communicating with the chamber for supplying a stream of reaction gas thereto, and an RF means including a driven and receiver antenna pair with an annular antenna around the chamber and a planer antenna associated with the end wall of the chamber.

5 Claims, 2 Drawing Figures

APPARATUS FOR LOW TEMPERATURE ASHING USING RADIO FREQUENCY EXCITED GAS PLASMA

BACKGROUND OF THE INVENTION

This invention relates generally to radio frequency (RF) excited gas plasma reaction devices and more particularly to a reaction device to low temperature ashing of organic specimens prior to trace element analysis.

In the laboratory techniques of analysis of inorganic content of organic substances, various means have been used to decompose the organic substance so that the residual inorganic content may be analyzed. Among these, the method of wet ashing is widely used to decompose the organic constituents of the sample. In the wet ashing process, relatively large quantities of hot mineral acids are used for the decomposition process. Aside from the complexity of handling the large quantities of acid and the attendant danger in conducting the process, the technique suffers the disadvantage that the acids used must be extremely pure, otherwise contaminants in the acids will reduce the accuracy of the analysis being made. Furthermore, with the wet digestion process, an operator must be present at all times during the process to deal with foaming, bumping, spattering, and so forth.

Due to the disadvantages of the wet digestion process and requirement for more accurate determination of trace elements in organics, there was a requirement for other methods of reduction of organics to produce the required data. Among these, the most promising has been the use of a plasma for low temperature reduction of organics. In this technique, a reaction gas, such for example as oxygen, is coupled to the output of an isolater operating at radio frequencies in a chamber to form a plasma which then reacts with the organic substance to reduce that substance to ash at low temperature. Chemical changes are brought about at relatively low temperatures in the organic materials by chemically active neutral species which are produced by excitation of the low pressure gas by the RF electric field. The chemically active neutral species are produced in the field through the collision of accelerated ions and electrons with neutral gas molecules. The active species are relatively susceptible to recombination or destruction, particularly by contacting the walls of the containing chamber. The rate of destruction of the active species at the walls is directly dependent upon the wall temperature and it is therefore important that the temperature of the walls of the chamber be maintained as low as is possible.

There are, in the prior art, several devices which accomplish the general objectives of low temperature ashing of organic substances through the use of an RF plasma. Among the disadvantages of the prior art devices are the requirements for an inordinately high power to accomplish the required ashing of organics with the resultant increase or inordinately high level of temperature of the reaction chamber walls. This requires that special care be taken to minimize the contact of the plasma with the chamber walls so that destruction of the active species will be kept at a minimum.

Of the prior patents and publications noted pertaining to the invention, the patent to Bersin, U.S. Pat. No. 3,410,776; the patent to Gleit, U.S. Pat. No. 3,547,802; and two publications, Chester E. Gleit and Walter D. Holland, "Use of Electrically Excited Oxygen for the Low Temperature Decomposition of Organic Substances," *Analytical Chemistry*, 34:1454 (1962), and Chester E. Gleit, "High Frequency Electrodeless Discharge System for Ashing Organic Matter," *Analytical Chemistry*, 37:314 (1965); the patent to Gorin, U.S. Pat. No. 3,775,621; and the patent to Mitzel, U.S. Pat. No. 3,875,068 all relate to RF gas plasma reduction apparatus of a type having a helical or solenoid antenna around the reduction chamber. As will be discussed in greater detail below, this type of antenna and approach to formation of the plasma is relatively inefficient and requires large input of energy to obtain the required reduction of organic substances. The prior art patents to Hollahan, U.S. Pat. No. 3,428,548, Gorin, U.S. Pat. No. 3,619,403, and Bersin, U.S. Pat. Nos. 3,647,676 and 3,671,195 relate to gas plasma devices having split antennas. This type of antenna has the disadvantage of imparting undue heating to the walls of the reduction chamber with the attendant disadvantages of destruction of active species set forth above. The patent to MacLean, U.S. Pat. No. 3,205,162 relates to a liquid cooling apparatus for an electric discharge process somewhat similar to a cooling device disclosed in the present invention. This reference is distinguished over the present invention in that the equivalent of the "antenna" for MacLean is within the cooling device with attendant disadvantages to be discussed in detail hereinafter.

SUMMARY OF THE INVENTION

This invention provides a method and apparatus for reducing the an ash organic specimens which avoids the disadvantages of the prior art wet ashing process by incorporating a low temperature "dry" process utilizing a gas plasma which reduces the quantity of acid required in reduction thereby reducing the danger to the operator from handling the acid and from the volatile fumes generated be the reduction process, reduces the requirement for operator attendance in that the process is relatively straightforward without foaming, bumping, spattering, and the like, and the process is fairly gentle so that metals will not be lost if the device operates after all of the organic material has reacted. The gas plasma method also reduces the possibility of injection of contaminants into the reaction chamber thereby allowing analysis of very minor trace elements in the specimen.

The invention also provides an improved gas plasma reduction process which operates with greater efficiency and less energy input required by providing a new combination of apparatus and antenna configuration.

Further advantages include the provision of a means to maintain the temperature of the reactor chamber walls at a minimum without reducing the efficiency of the RF antenna system, means for agitating the specimen to present the maximum surface area for reaction at all times, and a method for pretreating the specimen prior to introduction into the chamber to reduce the time and energy required to completely ash the specimen.

In a preferred embodiment the invention comprises a low temperature ashing device having side and end walls defining a gas-tight reaction chamber, means communicating with the chamber for reducing the pressure therein, means communicating with the chamber for supplying a stream of reaction gas thereto, a radio frequency means coupled to the gas to generate a plasma and produce low temperature ashing of a specimen in the chamber, the radio frequency means including a driven and receiver antenna pair with an annular antenna encompassing the side walls of the chamber and a planer antenna spaced from the annular and associated with one of the end walls of the chamber.

These and other advantages and many of the objectives of the invention will become better understood to those skilled in the art by reference to the following detailed description when viewed in light of the accompanying drawings wherein like components throughout the figures thereof are indicated by like numerals and wherein:

DESCRIPTION OF A PREFERRED EMBODIMENT

It should be understood that, although specifically described hereinbelow, the invention includes a water jacket for cooling, the invention may be practiced in certain applications without the need of a water coolant or the requirement for a cooling jacket actually installed in the vessel. As will readily be seen, the device as described hereinbelow could function mechanically and electrically as well without the inclusion of the water jacket.

Figure 1:
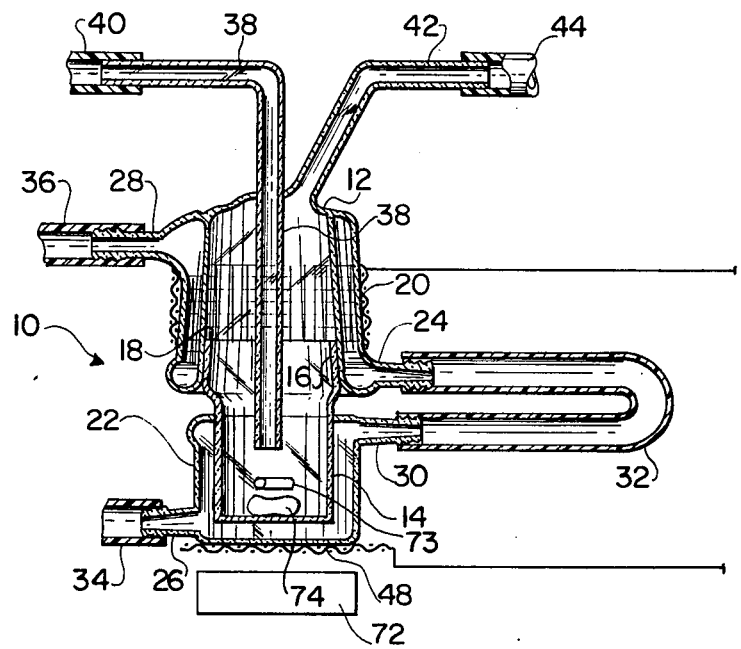
FIG. 1 is an elevational view end section of an apparatus in accordance with the invention.

Referring now to FIG. 1 of the drawings, the cell indicated generally at 10 comprises cup-shaped top and bottom portions 12 and 14, respectively. These cells are preferably constructed of pyrex or an equivalent material with low coefficient of expansion. Connection between the top and bottom portions of the cell 12 and 14 is achieved using a standard taper (45/50) ground glass joint preferably with the cell top 12 forming the outer 45/50 ground glass joint 16 at its lower opening and the bottom cell 14 having an outer or male ground glass joint 18 at its upper periphery. Water jackets 20 and 22 are formed around the top and bottom cells 12 and 14, respectively, and are provided with water inlets 24 and 26 and water discharge nipples 28 and 30, respectively. Using a flexible tubing such as latex or the like, the discharge 30 from the lower water jacket is connected to the inlet 24 of the upper water jacket by a hose 32 after the top and bottom portions of the cell 12 and 14 have been assembled. The lower inlet 26 is connected to a source of cooling water (not shown) through a hose 34 while the upper discharge 28 is connected to a receiver (not shown) through another discharge hose 36.

Figure 2:
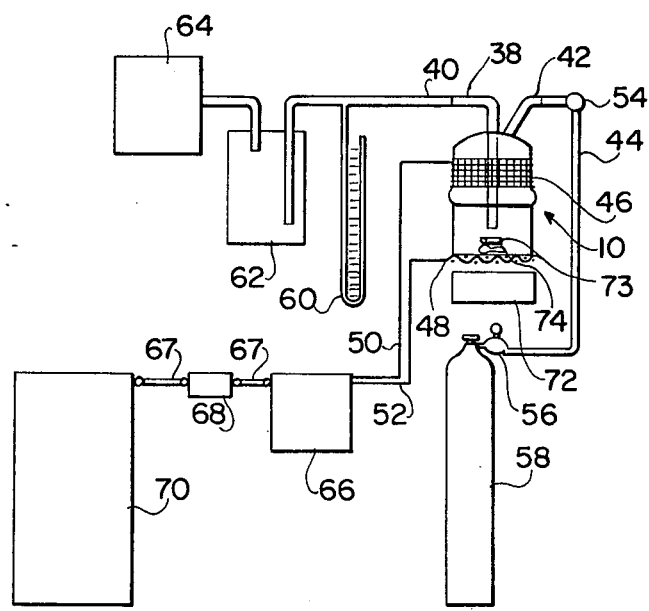
FIG. 2 is a schematic of a system incorporating the device of FIG. 1.

A gas inlet tube 42 communicates with the upper end of the top cell 12 and communicates with a source of gas through a supply hose 44. Tubing 38 extends downwardly through the top cell 12 such that the end thereof is in proximity to the inside bottom of the bottom cell 14 for purposes to be described below. A vacuum hose 40 connects the tubing 38 with a source of vacuum (Fig. 2). The tubing should preferably be made of a 6–8 millimeter glass stock and, with the components assembled, the assembly annealed in an oven for at least 24 hours.

The radio frequency excitation is applied to the cell through an antenna pair comprising an annular antenna 46 encompassing the side walls of the top cells 12 and a planer antenna 48 disposed beneath the bottom end of the bottom cell 14 as shown. The antennas are preferably in the form of an open mesh made of copper screening or the like and are connectable to a radio frequency oscillator for excitation through conductors 50 and 52, respectively.

In FIG. 2, the water jacket system is omitted from the cell 10 for purposes of clarity.

In that figure, the cell 10 is illustrated connected into the system for supplying the various constituents for operating the cell. In the figure, the gas is supplied to the tubing 42 through the hose 44 which is connected by a valve 54 to a pressure regulator 56 for connection in turn to a source of gas in the pressurized bottle 58. Vacuum is applied to the interior of the cell 10 through the tubing 38 and vacuum hose 40 which is connected through a manometer 60 and a cold trap 62 to a pump 64. The antennas 46 and 48 are connected through the conductors 50 and 52 to an antenna tuner 66 and through coaxial cables 67 to a standing wave ratio bridge 68 and a radio frequency oscillator/driver 70. The cell 10 and antenna 48 are mounted over a magnetic stirring device 72 to be described in greater detail below.

The radio frequency oscillator/driver 70 can be selected from existing oscillators and amplifiers manufactured and currently on the market and that suit the needs of the cell. As an example, transmitter operating with a crystal controlled pulsed output at 27.12 MHz with the output power controlled by varying the pulse frequency or screen voltage has been found suitable. Transmitter has a maximum pulse frequency of 600 pulses per second with each pulse having a duration of approximately 65 microseconds. The average power input of the transmitter as received is 37.5 watts when operated at maximum pulse frequency and power. The control circuitry of the unit used was modified to extend the pulse with a decreased screen voltage and a power input increase of 2.5 times the original power was realized.

The antenna configuration of the present invention has proved to be extremely efficient and has proved to produce heating less than that in other antenna configurations. As an example, the antenna pair comprising the annular antenna 46 and the planar antenna 48 was compared in laboratory tests to two other antenna configurations; the solenoid (helical) antenna and the loop to ground plane antenna which involves a circular antenna constructed from an 8-inch copper tubing used in conjunction with the planer screen antenna at the bottom of the cell. In the test, the solenoid antenna did not produce appreciable ashing of the filter paper and the loop antenna caused a major heating problem so that the ash-rate studies could not be adequately carried out. Comparative pressure flow relationships for the three different antenna configurations are listed below in Table I:

TABLE I

Ashing of Filter Paper by Low Temperature Ashing Relationships of Pressure and Flow to Ash Rate Power - 37.5 watts Freq. - 27.12 MHz
0.5 gm S & S ashless filter paper in cell

| Antenna  | Pressure | Flow | Ash Rate  |
|----------|----------|------|-----------|
| Solenoid | 1.7 mm   | —    | 64 mg/hr  |
|          | 1.7 mm   | —    | 47 mg/hr  |

TABLE I-continued

Ashing of Filter Paper by Low Temperature Ashing
Relationships of Pressure and Flow to Ash Rate Power - 37.5 watts Freq. - 27.12 MHz
0.5 gm S & S ashless filter paper in cell

| Antenna | Pressure | Flow | Ash Rate |
| --- | --- | --- | --- |
| | 1.0 mm | — | 76 mg/hr |
| Loop to | 1.5 mm | 8 ml/min | 118 mg/hr |
| Ground Plane | | | |
| Circular Screen | 1.5 mm | 8 ml/min | 300 mg/hr |
| to Ground Plane | 2.0 mm | 13 ml/min | 369 mg/hr |
| | 3.0 mm | 26 ml/min | 404 mg/hr |
| | 3.0 mm | 30 ml/min | 465 mg/hr |
| | 4.5 mm | 40 ml/min | 358 mg/hr |

As can be seen from the comparative tests, the antenna configuration of the present invention (the circular screen to ground plane) produces ash rate substantially greater than 2 to 3 times that of the comparative antenna configurations.

In operation, the specimen is placed in the bottom cell 14 and the surfaces of the ground joints 16 and 18 are coated with stopcock grease. The top and bottom cells 12 and 14 are then joined and the cell is secured mechanically with the gas inlet tubing 38 sealed from the atmosphere by means of closing the valve 54 (FIG. 2). The pump 64 is started and the pressure within the cell 10 is reduced to less than 3 mm of mercury. Cooling water is turned on to flow through the hose 34, inlet nipple 26 through the lower water jacket 22 and hose 32 into the upper water jacket returning through the discharge hose 36 to receiver. The flow should be at about 0.2 to 0.3 gallons per minute. The transmitter 70 was then activated and the antenna tuner 66 is adjusted for the best match of load and line (Standing Wave Ratio less than 2.5:1). After ignition occurs in the chamber (evidenced by emission of light), the valve 54 is opened to allow emission of gas from the bottle 58 into the cell. In this instance, the gas comprises pure oxygen properly pressure regulated through the regulater 56. Flow rate of the oxygen into the cell 10 should be about 30 cc/min. The tuning network should then again be adjusted to tuned for minimum Standing Wave Ratio. The magnetic stirrer 72 is then activated to remove surface ash from the specimen 74 and the device is operated until the specimen is completely ashed and only white powder remains in the cell. The radio frequency generator 70 is then turned off and the vacuum line out is closed. The cell is allowed to reach atmospheric pressure by gas bled in through the gas inlet tube 42 and the top of the cell 12 is removed from the bottom of the cell 14, the sample ash dissolved and removed.

One of the problems with the apparatus used for low temperature ashing is lack of agitation and mixing in the sample chamber. Oxidation rate is a function of exposed surface and decreases markedly as the surface becomes covered with mineral residue. The buildup of mineral coating causes a decrease in ash rate and when all of the sample is coated, ashing ceases for all practical purposes. The magnetic stirring device 72 comprises a magnetic drive beneath the cell 10 which rotates a stirring bar 73 within the cell 10 on the sample or specimen 74. The bar 73 within the cell, driven by a rotating field from the drive, works as a roller to remove some of the surface ashes and salt from the specimen in the process of ashing. The radio frequency used to generate the plasma is of a sufficiently high frequency so that it does not cause molecular randomization in the bar 73 as would low frequency alternating current.

It was determined that the placement of the annular antenna, viz. the water cooling cell, was important in that tests were made wherein the antenna was placed inside the water jacket to reduce the distance between the antenna and the reaction chamber. A cell constructed with an interior annular antenna was first tested without the cooling water in the jacket and it was found that the cell operation was substantially the same with the ash rate being substantially the same as with the antenna placed external of the water jacket. When water was introduced into the water jacket, the tuning network had to be modified to compensate for the lower impedance of the antenna when it was covered with cooling water. The ash rate of the cell with the antenna immersed in the cooling water was found to be only 10 percent that of an unjacketed cell. A sample of NBS orchard leaves (1.5 grams) was ashed in this cell for 38 hours at 37.5 watts in a pressure of 2 mm. At the end of this time, there was considerable unashed material remaining in the cell. It was therefore determined, in spite of the larger distance between the annular antenna and the interior of the cell with an externally placed annular antenna on the water jacket, the placement of that antenna exteriorly of the water jacket is beneficial.

The specimen salt and metals are then dissolved in a small portion of mineral acid and the residual metals are analyzed. The water-cooled cell allows higher power inputs if tests are being made for the most volatile metals and, according to Gleit and Holland, most metals are retained in the reaction chamber.

In the wet digestion procedure, 50–100 ml of acid must be used and all reagents used in the wet digestion process must be ultra pure because evaporation of any of the digest will increase the concentration of impurities.

The reagent cost for determination will be less by the present method than by wet digestion particularly if ultra pure acids are necessary. Purification of reagents in the laboratory for low temperature ashing by distillation or electrodeposition is feasible and practical because of the small volumes needed in the present process. Cost and time necessary to prepare large volumes of reagents used in wet digestion are prohibitive if in-house purification must be done.

During low temperature ashing with the present process, only minimal ventilation is required because any toxic fumes, if produced, are trapped in a Dewar Trap. Large volumes of hot acids used for wet digestion are not needed with low temperature ashing. With proper interlocks and shielding, the operator will not be exposed to the radio frequency emission or high voltage.

Once a low temperature ashing device is in operation, there is no need for constant operator attendance. The capacitance and inductance of the cell does not change as the sample ashes. With wet digestion, an operator must be present to deal with foaming, bumping, spattering, etc. Since low temperature ashing is a fairly gentle method of destruction, metals should not be lost if a device operates after the organic material has reacted.

Some of the reasons that the present invention provides an improvement over prior art devices such as that proposed by Gleit et al in the Analytical Chemistry, 34:1454 (1962) is that the chamber of the present cell incorporates increased density radio frequency fields enabling more plasma to be created with low power levels. Plasma is directed so that it is in intimate contact with the specimen being ashed. The specimen has a maximum surface free from mineral and salt residue when the magnetic stirrer is used. Furthermore, the gas flow dynamics are such that the distance traveled by the active species from the excitation point is kept as short as possible, thereby minimizing de-excitation reactions between species (excitation virtually cell wide). Ashing pressures are kept high (2-5 mm) so that the energy is imparted to the gas plasma and not to the kinetic energy of the electrons as happens where the ashing pressure must be lower.

Utilizing a commercial low temperature ashing of a type currently on the market, the results in Table II below were obtained for the commodities listed.

TABLE II

| Sample | Wt. Sample | Time | Ash and Carbon Remaining |
|---|---|---|---|
| Canned Green Beans (drained, not dried) | 4.32 gm | 2¼ hr | 2% |
| Canned Green Beans (dried and ground) | 1.00 gm | 10 hr | 57% |
| Catfish (raw, frozen) | 4.77 gm | 6 hr | 1.4% |
| Mushrooms (drained) | 1.29 gm | 8 hr | .5% |
| Polish Sausage (ground, not dried) | 6.84 gm | 12 hr | incomplete ash |
| Northern Pike | 12.84 gm | 8–12 hr | incomplete ash |
| Halibut (chunk of raw fish) | 17.07 gm | 8–12 hr | incomplete ash |

This instrument had a single chamber with an RF driver capable of 150 watts intermittent and 100 watts continuous duty. Samples other than those in the table were attempted but in all cases, including the above, it was not possible to get complete ash even when mixing. When the residue was dissolved in acid, small clumps of carbon were present.

The low temperature ashing vessel in accordance with Gleit and Holland (ante), using a linear flow chamber and solenoid antenna, was duplicated. Using a BC 610 transmitter delivering about 200 watts to the linear chamber and operating for about 30 minutes, charring of the sample and excessive cell heating resulted. Results of testing with comparative low temperature ashing units revealed several problems:

a. There was an inability to take the specimens to complete ash in a reasonable time.

b. Heating problems of the specimen were considerable and reliable data on the recovery of the more volatile metals was not available. Even where the chamber was cooled by an external fan, the transfer of heat from the specimen could not take place because of the insulating vacuum present.

c. Handling of the sample was considerable. In the commercial unit obtained the container had to be placed in a reaction chamber, the unit operated until all exposed surfaces had reacted, the chamber pressurized and sample removed, the sample stirred and the steps repeated until a usable ash remained.

d. The reaction chamber was fairly large and only random drift was utilized to bring the plasma into contact with the specimen; i.e., there was no directional flow of the active gas.

e. In order to minimize the recombination of the active species with gas molecules, pressure had to be kept at a low level (0.5 Torr). When operating at this pressure, most radio frequency energy imparted to the gas is carried off as kinetic energy by free electrons and a lesser amount to the formation of the active atomic species.

It was found that the ashing times could be reduced substantially by proper pre-preparation of the specimens. It was found that, where the specimens were freeze dried prior to ashing, the ashing times required were substantially lessened. As a comparison, samples of drained green beans (unground and undried) were run. The sample (8.57 grams) was run at 37.5 watts and 3 mm pressure in an unjacketed cell. After 5.5 hours of operation, the sample appeared to be completely ashed. Residue weighed 0.27 grams representing 3.2% of the product. When the ash was dissolved in 5 ml of N/10 HCl, undissolved residue represented 0.94% of the original sample weight.

The freeze dried beans initially contained 93.4% moisture. A portion of freeze dried beans representing 8.39 grams of original product was ashed under conditions identical to the above. After 2.5 hours, all the material remaining in the cell appeared to be white powder and weighed 0.18 gram representing 2.2% of product. The residue in the ash weighed 0.013 grams or 0.15% of product weight.

As a result of the reduction in ashing time and completeness of ashing utilizing the freeze dried pre-prepared products, experiments were conducted with preliminary freeze drying of other canned vegetables.

Five different canned vegetables were selected for the rate study. These commodities are of the "low acid" type and all samples except the cream style corn were drained before freeze drying. Each sample ashed represents 8–12 grams of drained product.

TABLE III

| Product | % Moisture | Ash Rate Whole Product | Dry Residue |
|---|---|---|---|
| Green Beans | 93.41 | 2.4 gm/hr | 158 mg/hr |
| Carrots (diced) | 93.98 | 3.1 gm/hr | 188 mg/hr |
| Butter Beans | 71.88 | 1.2 gm/hr | 388 mg/hr |
| Peas | 83.34 | 1.9 gm/hr | 309 mg/hr |
| Cream Style Corn | 80.03 | 1.3 mg/hr | 252 mg/hr |
| Power 37.5 watts | Freq. 27.1 MHz | Pressure 3 mm Hg | |

The method and apparatus presented by the present invention provides a simple and direct low temperature ashing when used for digestion of organics. The only source of contamination to be considered is the acid used when dissolving the ash. The process presented is a particularly useful tool where scientists, doctors, and government officials will need a reliable and accurate quantitation of ultra low level metal contamination in foods. The absence of reagent contamination is a prime factor recommending low temperature ashing over conventional digestion techniques especially where the very low level quantitation is attempted and the requirement for low energy input and high efficiency of digestion recommends this low temperature ashing process and apparatus over other less efficient, complete and more time and energy consuming processes and devices.

What is new and desired to be protected by Letters Patent of the United States is:

1. A low temperature ashing device comprising:
    side and end walls defining a gas tight reaction chamber for containing a specimen to be ashed;
    means communicating with said chamber for reducing the pressure therein;
    means communicating with said chamber for supplying a stream of reaction gas thereto; and
    RF means for coupling a radio frequency output to said gas and generating a plasma to produce low temperature ashing of a specimen therein, said RF means including a driven and receiving antenna pair having an annular antenna encompassing the side walls with a spaced substantially planer antenna associated with an end wall of said chamber.

2. The low temperature ashing device in accordance with claim 1 wherein said chamber is substantially cylindrical and of a height substantially on the order of 2 times the diameter thereof.

3. The low temperature ashing device in accordance with claim 2 wherein said chamber comprises two substantially equal cylindrical chamber halves removably joined together by means of a tapered ground joint therebetween.

4. The low temperature ashing device in accordance with claim 1 further comprising an annular water jacket disposed around said chamber for cooling thereof, means to circulate water through said chamber and wherein said annular antenna is disposed around the exterior of said water jacket.

5. The low temperature ashing device in accordance with claim 1 further comprising specimen stirring means including a stirring bar disposed within said chamber and a magnetic drive exterior of said chamber to induce rotation of said stirring bar.

* * * * *